US00PP27655P3

(12) United States Plant Patent
Danziger

(10) Patent No.: US PP27,655 P3
(45) Date of Patent: Feb. 7, 2017

(54) ***SUTERA* PLANT NAMED 'DCOPGPKHRT'**

(50) Latin Name: *Sutera cordata*
Varietal Denomination: DCOPGPKHRT

(71) Applicant: Gavriel Danziger, Moshav Mishmar Hashiva (IL)

(72) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 64 days.

(21) Appl. No.: 14/545,461

(22) Filed: May 7, 2015

(65) Prior Publication Data

US 2016/0330898 P1 Nov. 10, 2016

(51) Int. Cl.
*A01H 5/02* (2006.01)

(52) U.S. Cl.
USPC ..... Plt./485

(58) Field of Classification Search
USPC ..... Plt./485
See application file for complete search history.

*Primary Examiner* — Anne Grunberg
(74) *Attorney, Agent, or Firm* — Cassandra Bright

(57) ABSTRACT

A new and distinct *Sutera* cultivar named 'DCOPGPKHRT' is disclosed, characterized by abundant extra-large light pink flowers with a violet center. Plants are of moderate vigor, mounded, well branched and begin flowering early. The new variety is a *Sutera*, normally produced as an outdoor garden or container plant.

2 Drawing Sheets

Figure 1:
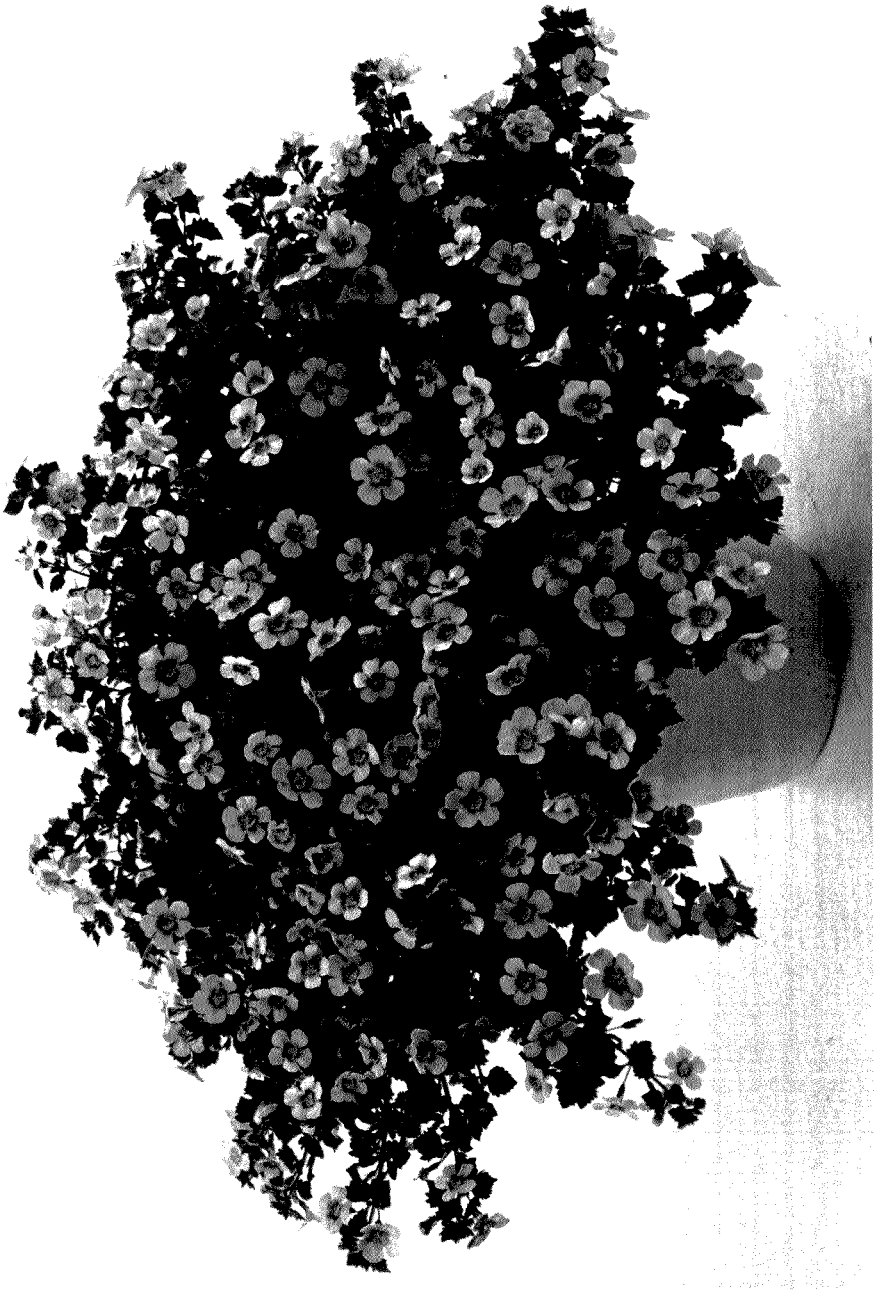

Latin name of the genus and species: *Sutera cordata*.
Variety denomination: 'DCOPGPKHRT'.

BACKGROUND OF THE INVENTION

The new *Sutera* cultivar is a product of a planned breeding program conducted by the inventor, Gavriel Danziger, in Moshav Mishmar Hashiva, Israel. The objective of the breeding program was to produce new *Sutera* varieties for ornamental commercial applications. The open pollination resulting in this new variety was made during September of 2011.

The seed parent is the, unpatented, proprietary variety referred to as *Sutera* 'cv. 11-1892'. The pollen parent is unknown as it was an open pollination breeding program. The new variety was discovered in May of 2012 by the inventor in a group of seedlings resulting from the 2011 crossing, in a research greenhouse in Moshav Mishmar Hashiva, Israel.

Asexual reproduction of the new cultivar was performed by vegetative cuttings. This was first performed at a research greenhouse in Moshav Mishmar Hashiva, Israel in May of 2012 and has shown that the unique features of this cultivar are stable and reproduced true to type in more than 20 successive generations.

SUMMARY OF THE INVENTION

The cultivar 'DCOPGPKHRT' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DCOPGPKHRT' These characteristics in combination distinguish 'DCOPGPKHRT' as a new and distinct *Sutera* cultivar:

1. Mounded growth habit.
2. Extra-large, light pink flowers with a violet center.
3. Well branched plant
4. Early, abundant flowering.
5. Moderate vigor.

Plants of the new cultivar 'DCOPGPKHRT' are similar to plants of the seed parent, *Sutera* 'cv. 11-1892' in most horticultural characteristics, however, plants of the new cultivar 'DCOPGPKHRT' differ in the following;

1. Plant habit is mounded. The parent habit is semi-trailing.
2. Larger flowers than the parent variety.
3. More abundant flowering than the parent variety.
4. Well branched form. The parent variety produces less branches per plant.
5. Less vigor than the parent variety.

COMMERCIAL COMPARISON

Plants of the new cultivar 'DCOPGPKHRT' are comparable to the patented commercial variety *Sutera* 'DANDCOP27' U.S. Plant Pat. No. 19,782. The two *Sutera* varieties are similar in most horticultural characteristics; however, the new variety 'DCOPGPKHRT' differs in the following:

1. Comparison variety has a semi-trailing growth habit whereas 'DCOPGPKHRT' has a mounded growth habit.
2. Comparison variety has large, light pink flowers with a violet center, whereas 'DCOPGPKHRT' has an extra-large, light pink flowers with a violet center.
3. Comparison variety produces more branches per plant than 'DCOPGPKHRT'.
4. Comparison variety has strong vigor whereas 'DCOPGPKHRT' has moderate vigor.

Plants of the new cultivar 'DCOPGPKHRT' can also be comparable to the unpatented commercial variety *Sutera* 'DANCOP102'. The two *Sutera* varieties are similar in most horticultural characteristics; however, the new variety 'DCOPGPKHRT' differs in the following:

1. Comparison variety has a semi-trailing growth habit whereas 'DCOPGPKHRT' has a mounded growth habit
2. Comparison variety has extra-large, white flowers whereas 'DCOPGPKHRT' has extra-large, light pink flowers with a violet center.
3 Candidate variety produces less branches than 'DCOPGPKHRT'.
4. Comparison variety has strong vigor whereas 'DCOPGPKHRT' has moderate vigor.

BRIEF DESCRIPTION OF THE PHOTOGRAPHS

The accompanying photograph in FIG. 1 illustrates in full color a typical plant of 'DCOPGPKHRT' grown in a greenhouse, in a 13 cm pot. Age of the plant photographed is approximately 3 months old from a rooted cutting.

Figure 2:
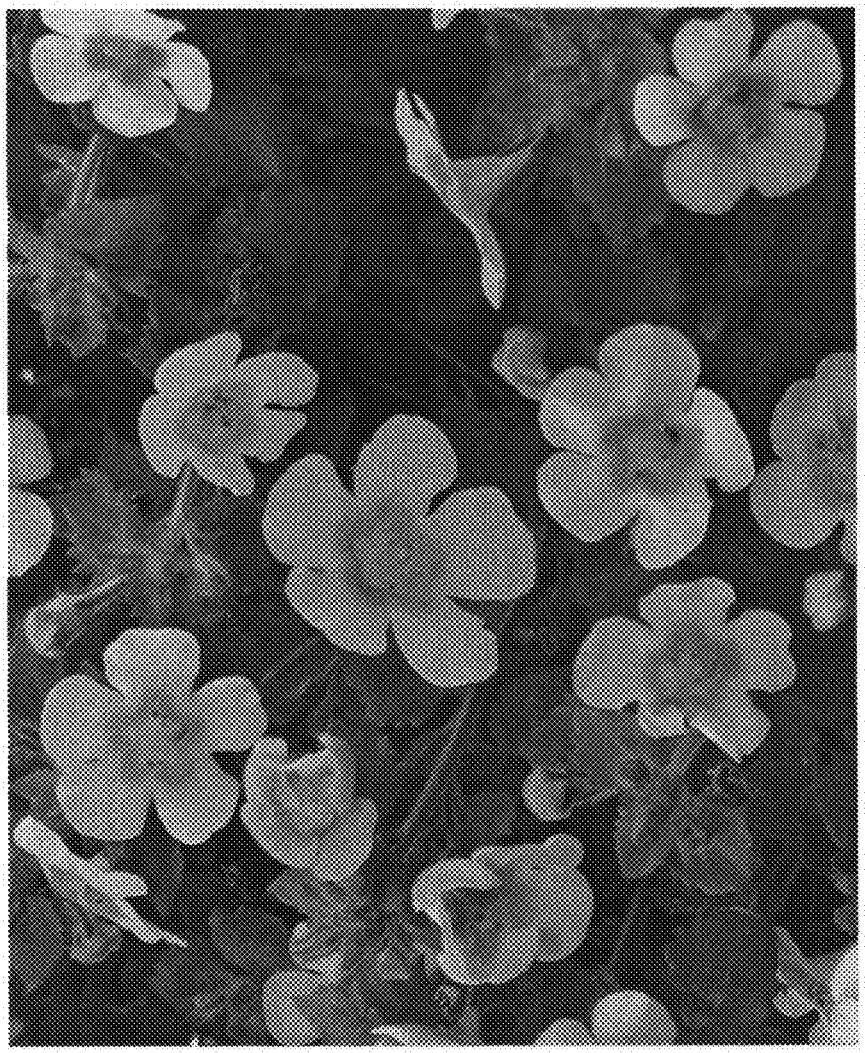

FIG. 2 illustrates a close up of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2001 except where general terms of ordinary dictionary significance are used. The following observations and measurements describe 'DCOPGPKHRT' plants grown in the Winter to Spring in moderate climate in a greenhouse, in Moshav Mishmar Hashiva, Israel. The growing temperature ranged from 15° C. to 26° C. during the day and from 13° C. to 16° C. during the night. General light conditions are normal sunlight and numerical values represent averages of typical plant types.

Botanical classification: *Sutera cordata* 'DCOPGPKHRT'.

PROPAGATION

Type of propagation typically used: Cutting.
Time to initiate roots: 7-10 days at approximately 20° C.
Root description: Fine, fibrous roots.

PLANT

Age of plant described: Approximately 3 months from rooted cutting.
Container size of the plant described: 13 cm.
Growth habit: Mounded.
Height: Approximately 16 cm.
Plant spread: Approximately 50 cm.
Growth rate: Medium.
Characteristics of primary lateral branches:
- *Quantity*.—About 8.
- *Form*.—Cylindrical.
- *Length*.—About 25 cm.
- *Diameter*.—About 0.2 cm.
- *Color*.—RHS Yellow-Green 146 B.
- *Texture*.—Velvety.
- *Strength*.—Strong and flexible.

Internode length: About 2 cm.

FOLIAGE

Leaf:
- *Arrangement*.—Opposite, petiolate.
- *Quantity*.—Approximately 60 per branch.
- *Average length*.—3 cm.
- *Average width*.—2.5 cm.
- *Shape of blade*.—Ovate.
- *Apex*.—Obtuse.
- *Base*.—Acuminate.
- *Margin*.—Serrate.
- *Texture of top surface*.—Velvety.
- *Texture of bottom surface*.—Velvety.
- *Pubescence*.—Slightly pubescent all surfaces.
- *Aspect*.—About 90° angle of attachment to branch, flat leaf.
- *Color*.—Young foliage upper side: RHS Green 137 B. Young foliage under side: RHS Green 137 C. Mature foliage upper side: RHS Green 137 A. Mature foliage under side: RHS Green 137 B.
- *Venation*.—Type: Pinnate. Venation color upper side: RHS Green 137 A. Venation color under side: RHS Green 137 C.
- *Petiole*.—Length: About 0.5 cm. Diameter: About 0.2 cm. Color: RHS Green 137 A.
- *Texture*.—Slightly velvety.

FLOWER

Natural flowering season: All year round in Israel.
Days to flowering from rooted cutting: About 45.
Inflorescence and flower type and habit: Axillary, solitary, salverform single flowers.
Rate of flower opening: 3 to 5 days from bud to fully opened flower.
Flower longevity on plant: About 7 days.
Persistent or self-cleaning: Persistent.
Bud:
- *Shape*.—Spatulate.
- *Length*.—About 1.5 cm.
- *Diameter*.—About 0.8 cm.
- *Color*.—RHS Purple 75 B.

Flower size:
- *Diameter*.—About 2.8 cm.
- *Length*.—About 1.7 cm.
- *Corolla tube diameter*.—About 0.4 cm.

Corolla/petals:
- *Arrangement*.—Symmetric.
- *Lobe length*.—About 1 cm.
- *Lobe width*.—About 1.3 cm.
- *Quantity*.—5.
- *Texture*.—Velvety.
- *Lobe apex*.—Rounded.
- *Lobe shape*.—Rounded.
- *Margin*.—Entire.
- *Aspect*.—About 90° to the tube.

Color:
- *When opening*.—Upper surface: RHS Purple 76 B. With a Purple center: RHS Purple N78 B. Lower surface: RHS Purple 76 C.
- *Fully opened*.—Upper surface: RHS Purple 76 B. With a Purple center: RHS Purple N78 C. Lower surface: RHS Purple 76 C.
- *Visible corolla tube color*.—RHS Yellow-Orange 14 A.

Calyx/sepals:
*Quantity per flower.*—5.
*Shape*.—Linear.
*Length*.—About 0.8 cm.
*Width*.—About 0.1 cm.
*Apex*.—Acute.
*Base*.—Fused.
*Margin*.—Entire.
*Texture*.—Slightly velvety.
*Color*.—Upper Surface: RHS Green 137 A. Lower Surface: RHS Green 137 B.

Peduncle: None.

Pedicel:
*Length*.—Approximately 1.3 cm.
*Diameter*.—Approximately 0.1 cm.
*Color*.—Near RHS Green 137 B.
*Orientation*.—Slanted upward and outward.
*Pubescence*.—Slightly pubescent.

Fragrance: None.

REPRODUCTIVE ORGANS

Stamens:
*Number.*—4.
*Filament length*.—Approximately 1.4 cm.

Anthers:
*Shape*.—Cylindrical.
*Length*.—Approximately 0.2 cm.
*Color*.—RHS Yellow-Orange 14 B.
*Pollen*.—Color: RHS Yellow-Orange 14 B. Quantity: Sparse.

Pistil:
*Number.*—1.
*Length*.—About 1.1 cm.
*Style*.—Length: About 1.2 cm. Color: RHS Yellow-Green 154 C.
*Stigma*.—Shape: Undulate. Color: RHS Yellow-Green 154 B. Ovary Color: RHS Green 138 A.

OTHER CHARACTERISTICS

Seeds and fruits: About 30 elliptic, small (1 mm long) Brown seeds per one elliptic Brown capsule. Minute, not accurately measured with R.H.S. chart.

Disease/pest resistance: Neither resistance nor susceptibility to normal diseases and pests of *Sutera* have been observed.

Temperature tolerance: Approximately 5° to 30° C.

What is claimed is:

1. A new and distinct cultivar of *Sutera* plant named 'DCOPGPKHRT' as herein illustrated and described.

* * * * *